United States Patent [19]
Bondinell et al.

[11] Patent Number: 6,121,290
[45] Date of Patent: Sep. 19, 2000

[54] USE OF GABA UPTAKE INHIBITORS AS ANTI-TUSSIVE AGENTS

[75] Inventors: William E. Bondinell, Wayne; Charles J. Kotzer, Hatboro; David C. Underwood, Ambler, all of Pa.

[73] Assignee: SmithKline Beecham Corporation, Philadelphia, Pa.

[21] Appl. No.: 09/194,325

[22] PCT Filed: May 23, 1997

[86] PCT No.: PCT/US97/08948

§ 371 Date: Mar. 17, 1999

§ 102(e) Date: Mar. 17, 1999

[87] PCT Pub. No.: WO97/43902

PCT Pub. Date: Nov. 27, 1997

Related U.S. Application Data

[60] Provisional application No. 60/018,258, May 24, 1996.

[51] Int. Cl.[7] .......................... A61K 31/445; A61K 31/38
[52] U.S. Cl. .......................... 514/317; 514/326; 514/444; 514/849; 514/850
[58] Field of Search ................................ 514/317, 326, 514/444, 849, 850

[56] References Cited

U.S. PATENT DOCUMENTS

| | | |
|---|---|---|
| 4,383,999 | 5/1983 | Bondinell et al. . |
| 4,514,414 | 4/1985 | Bondinell et al. . |
| 4,772,615 | 9/1988 | Pavia . |
| 5,006,560 | 4/1991 | Kreutner et al. . |
| 5,610,159 | 3/1997 | Moseley et al. . |

FOREIGN PATENT DOCUMENTS

| | | |
|---|---|---|
| WO 91/07389 | 5/1991 | WIPO . |
| WO 93/18143 | 9/1993 | WIPO . |
| WO 94/15618 | 7/1994 | WIPO . |
| WO 94/25027 | 11/1994 | WIPO . |

OTHER PUBLICATIONS

Bolser, et al., J. of Pharm. and Exp. Ther., 1995, vol. 274, No. 3, pp. 1393–1398.
Larsen, et al., Epilepsy Res., 1987, pp. 77–93.
Anderson, et al., J. Med. Chem., 1993, vol. 36, pp. 1716–1725.
Dhar, et al., J. Med. Chem., 1994, vol. 37, pp. 2334–2342.
Bolser, et al., Brit. J. of Pharm., 1994, vol. 113, pp. 1344–1348.
Ali, et al., J. Med. Chem., 1985, vol. 28, pp. 653–660.
Forsberg, et al., Acia Physiol Scand., 1986, vol. 128, pp. 319–320.
Laude, et al., Pulmonary Pharm., 1993, vol. 6, pp. 171–175.
Larsen, et al., Molecular & Cellular Bio., 1980, vol. 31, pp. 105–121.
Chapman, et al., TiPS, 1993, vol. 14, pp. 26–29.
Bolser, et al., Br. J. Pharmacol., 1993, vol. 110, pp. 491–495.
Yunger, et al., J. of Pharm. and Exp. Ther., 1984, vol. 228, No. 1, pp. 109–115.
Borden, et al., Eur. J. of Pharm., Mol. Pharm. Sec. 269, 1994, pp. 219–224.

*Primary Examiner*—Raymond Henley, III
*Attorney, Agent, or Firm*—Wayne J. Dustman; William T. King; Charles M. Kinzig

[57] ABSTRACT

Invention is a method of treating cough in a mammal, including a human, which comprises administering to such mammal an effective amount of an inhibitor of GABA uptake.

6 Claims, No Drawings

USE OF GABA UPTAKE INHIBITORS AS ANTI-TUSSIVE AGENTS

This application is a 371 of PCT/US97/08948 filed May 23, 1997, and also claims the benefit of U.S. Provisional application Ser. No. 60/018,258 filed May 24, 1996.

This invention relates to a method of treating cough in a mammal, including a human, in need thereof which comprises administering to such mammal an effective amount of an inhibitor of GABA uptake.

BACKGROUND OF THE INVENTION

Gamma-amino-butyric acid (GABA) is a major inhibitory neurotransmitter of the central and peripheral nervous systems and is released into the synapse on nerve stimulation where it can modulate the activity of other neurons. For most neurotransmitters, including GABA, neurotransmission is terminated by the rapid uptake of neurotransmitter via specific, high-affinity transporters located in the presynaptic terminal and/or surrounding glial cells. Kanner, B. I., et al., *Critical Review of Biochemistry;* CRC press; Boca Raton, Fla., 1987; Vol. 22, pp 1–38.

Compounds which inhibit GABA uptake have been shown to be useful in the treatment of anxiety, epilepsy, muscular and movement disorders and mental and emotional disorders (in U.S. Pat. No. 4,383,999), as well as demonstrating potent anticonvulsant effects (Yunger, L. M., et al., *J. Pharm. Exp. Ther.* 1985, 110, 418–427).

Presently, GABA uptake inhibitors are not known as having utility as anti-tussive agents.

SUMMARY OF THE INVENTION

This present invention resides in the discovery that compounds which inhibit GABA uptake have a therapeutic effect on treating cough in a mammal, including a human.

DETAILED DESCRIPTION OF THE INVENTION

All publications, including but not limited to patents and patent applications, cited in this specification are herein incorporated by reference as if each individual publication were specifically and individually indicated to be incorporated by reference herein as though fully set forth.

Compounds which inhibit GABA uptake are used in pharmaceutical compositions as anti-tussive agents.

Illustrative and preferred among the compounds that have GABA uptake inhibitory activity are the following.

A)

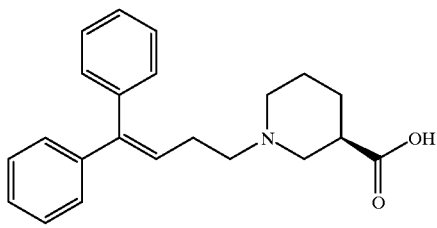

which is (R)-1-(4,4-diphenyl-3-butenyl)-3-piperidinecarboxylic acid. This compound is disclosed in U.S. Pat. No. 4,383,999, as having GABA uptake inhibitory activity.

B)

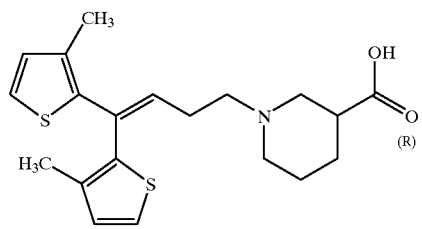

which is (R)-1-[4,4-bis(3-methyl-2-thienyl)-3-butenyl]-3-piperidinecarboxylic acid and which is disclosed in Anderson et al., *J. Med. Chem.* 36, (1993) 1716–1725 as having GABA uptake inhibitory activity.

C)

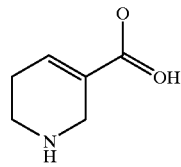

which is known as guvacine and which is disclosed in Krogsgaard-Larsen, *Molecular & Cellular Biochemistry* 31, 105–121 (1980) as having GABA uptake inhibitory activity.

Persons skilled in the art can readily determine if a compound is an inhibitor of GABA uptake by known methods such as those described in U.S. Pat. No. 4,383,999 and Ali, F. E., et al. *J. Med. Chem.* 1985, 28, 653–660. All such compounds are included within the scope of this invention.

By the term "treating" as used herein is meant prophylactic or therapeutic therapy.

By the term "inhibit GABA uptake" as used herein includes the uptake of GABA by the GABA nerve terminal, glial cells and any GABA cell surface transporter.

Compounds of the invention that inhibit GABA uptake were tested for their ability to inhibit cough in the general assay described in Forsberg, et al., *Respiration* 59: 72–76 (1992), with the following exceptions. Citric acid was nebulized for only one minute to the animals. Coughs were determined by examination of the flow signal and observation of the test animals.

The following compounds, described in Ali, F. E., et al. *J. Med. Chem.* 1985, 28, 653–660 as potent inhibitors of GABA uptake, were tested for in vivo potency as anti-tussive agents.

Compound 1—N-(4,4-diphenyl-3-butenyl)-3-pyrrolidineacetic acid [compound (1b) in Ali, F. E., et al. *J. Med. Chem.* 1985, 28, 653–660].

Compound 2—3-piperidinecarboxylic acid [compound (2a) in Ali, F. E. et al. *J. Med. Chem.* 1985, 28, 653–660].

Compound 3—(R)-N-(4,4-diphenyl-3-butenyl)-3-piperidinecarboxylic acid [compound (R)-(2b) in Ali, F. E., et al. *J. Med. Chem.* 1985, 28, 653–660].

Compound 4—1,2,5,6-tetrahydro-3-pyridinecarboxylic acid [compound (3a) in Ali, F. E., et al. *J. Med. Chem.* 1985, 28, 653–660].

Compound 5—N-(4,4-diphenyl-3-butenyl)-1,2,5,6-tetrahydro-3-pyridinecarboxylic acid [compound (3b) in Ali, F. E., et al. *J. Med. Chem.* 1985, 28, 653–660].

Compound 6—cis4-hydroxy-3-piperidinecarboxylic acid [compound (4a) in Ali, F. E., et al. *J. Med. Chem.* 1985, 28, 653–660].

To perform the experiments Male Hartley Guinea pigs weighing between 550, and 750 g were placed into a clear plastic exposure chamber with an internal volume of 6 l. A bias air flow was applied to the chamber at a flow rate of 2 l/min for the duration of the experiment. The changes in airflow inside the box were measured by use of pressure transducer MP 45-14 (Validyne Engineering Corp. Northridge, Calif.) that had a range of ±2 cm H20 and a pneumotach (consisting of nine 325-mesh screens) mounted on the top of the exposure chamber. Flow signals were output to a preamplifier bank (Buxco Electronics Inc. Sharon Conn.), and routed to a chart recorder (Linearcorder WR 3320 Western Graphtech, Irvine Calif.) for analyses.

An incidence of cough was denoted by a larger than normal inspiration (at least twice normal tidal deflection) followed immediately by a rapid, forceful expiration (more than three times the normal excursion from baseline). A cough was easily distinguished from animal movement, augmented breaths and gasps by close inspection of the data. Because a sneeze and cough have similar flow patterns, they were differentiated by visual observation of the animals.

Test compounds were administered via the IP route, and the pre-treatment time was 30 min. The aerosol was administered to the animals by connecting a small volume ultrasonic nebulizer (AeroSonic model 5000D Devilbis Sumerset, Pa.) to the bias-flow immediately before the exposure chamber inlet. The animals were challenged with 0.4M citric acid aerosol solution. A volume of 2 ml of citric acid solution was placed in the ultrasonic nebulizer. In one minute approximately 0.5 ml of the solution was nebulized to each animal. This has been previously shown to induce the cough reflex. The incidences of cough in 13 minutes (aerosolization time+observation time,) as well as time to onset of the first cough were recorded.

The guinea pigs treated with a GABA uptake inhibiting compound realized a significant decrease in the occurrence of cough. Thus, the administration of a GABA uptake inhibiting compound results in a therapeutic effect as an anti-tussive agent.

This invention discloses inhibitors of GABA uptake and pharmaceutically acceptable salts or hydrates or solvates thereof as being useful for treating cough in mammals, including humans.

An inhibitor of GABA uptake or a pharmaceutically acceptable salt or hydrate or solvate thereof can be administered to a subject in a conventional dosage form prepared by combining an inhibitor of GABA uptake or a pharmaceutically acceptable salt or hydrate or solvate thereof, with a conventional pharmaceutically acceptable carrier or diluent according to known techniques.

It will be recognized by one of skill in the art that the form and character of the pharmaceutically acceptable carrier or diluent is dictated by the amount of active ingredient with which it is to be combined, the route of administration and other well-known variables. An inhibitor of GABA uptake or a pharmaceutically acceptable salt or hydrate or solvate thereof is administered to a mammal, including a human, in an amount sufficient to prevent or alleviate cough.

The route of administration of the GABA uptake inhibitor is not critical but is usually oral or parenteral, preferably oral. Forms of parenteral administration include; intrarectal, transdermal, intravaginal or intraperitoneal administration. The subcutaneous and intramuscular forms of parenteral administration are generally preferred. The daily parenteral dosage regimen will be an efficacious, nontoxic quantity preferably selected from the range of about 0.001 mg/kg to about 20 mg/kg of total body weight, most preferably, from about 0.01 mg/kg to about 5 mg/kg. Preferably, each parenteral dosage unit will contain the active ingredient in an amount of from about 2 mg to about 150 mg.

The GABA uptake inhibitors which are active when given orally can be formulated as liquids, for example, syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavoring of coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

The daily oral dosage regimen will be an efficacious, nontoxic quantity preferably selected from the range of about 0.001 mg/kg to about 20 mg/kg of total body weight. Preferably each oral dosage unit will contain the active ingredient in an amount of from about 2 mg to about 150 mg.

While it is possible for an active ingredient to be administered alone, it is preferable to present it as a pharmaceutical formulation.

It will be recognized by one of skill in the art that the optimal quantity and spacing of individual dosages of an inhibitor of GABA uptake or a pharmaceutically acceptable salt or hydrate or solvate thereof will be determined by the nature and extent of the exact condition being treated, the form, route and site of administration, and the particular patient being treated, and that such optimums can be determined by conventional techniques. It will also be appreciated by one of skill in the art that the optimal course of treatment, i.e., the number of doses of a GABA uptake inhibitor or a pharmaceutically acceptable salt or hydrate or solvate thereof given per day and duration of therapy, can be ascertained by those skilled in the art of using conventional course of treatment determination tests.

The method of this invention of treating cough comprises administering to a subject in need thereof an effective amount of a GABA uptake inhibiting compound.

The invention also provides for the use of a GABA uptake inhibiting compound in the manufacture of a medicament for use as an anti-tussive agent.

The invention also provides for a pharmaceutical composition for use as an anti-tussive agent which comprises a GABA uptake inhibiting compound and a pharmaceutically acceptable carrier.

No unacceptable toxicological effects are expected when compounds of the invention are administered in accordance with the present invention.

Following are the results of testing the compounds of this invention.

TABLE I

| Cmpd # | Dose (mg) | Route | Control | Treated | % Inhibition | STE |
|---|---|---|---|---|---|---|
| Compound 1 | 20 | ip | 13.4 | 7.2 | 53.13 | 17.05 |
| Compound 2 | 20 | ip | 13.4 | 9.75 | 28.36 | 21.53 |
| Compound 3 | 1 | ip | 12.3 | 6.6 | 49.23 | 11.04 |
| " | 10 | ip | 13 | 2.8 | 78.46 | 5.65 |
| " | 10 | po | 14.2 | 8.2 | 42.25 | 10.06 |
| " | 30 | po | 14.2 | 8 | 43.66 | 11.78 |
| Compound 4 | 6 | ip | 14.7 | 7.6 | 48.30 | 10.67 |
| " | 20 | ip | 14.7 | 4.75 | 67.69 | 11.90 |
| Compound 5 | 1 | ip | 15.2 | 15.4 | 5.79 | 5.47 |
| " | 3 | ip | 15.2 | 12.4 | 20.53 | 9.12 |
| " | 30 | ip | 13.3 | 1 | 92.48 | 4.34 |
| Compound 6 | 10 | ip | 13.4 | 16.3 | 8.21 | 8.21 |
| " | 20 | ip | 13.4 | 8.6 | 35.82 | 5.58 |

The data in the above Table I demonstrates the therapeutic effect of GABA uptake inhibiting compounds as anti-tussive agents.

All of the compounds that are specifically disclosed herein are known and can be readily prepared by those of skill in the art. Notwithstanding, this invention relates to all GABA uptake inhibiting compounds.

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1

Capsule Composition

An oral dosage form for administering a GABA uptake inhibitor is produced by filing a standard two piece hard gelatin capsule with the ingredients in the proportions shown in Table I, below.

TABLE II

| INGREDIENTS | AMOUNTS |
|---|---|
| (R)-1-(4,4-diphenyl-3-butenyl)-3-piperidinecarboxylic acid | 25 mg |
| Lactose | 55 mg |
| Talc | 16 mg |
| Magnesium Stearate | 4 mg |

EXAMPLE 2

Injectable Parenteral Composition

An injectable form for administering a GABA uptake inhibitor is produced by stirring 1.5% by weight of (R)-1-[4,4-bis(3-methyl-2-thienyl)-e-butenyl]-3-piperidinecarboxylic acid in 10% by volume propylene glycol in water.

EXAMPLE 3

Tablet Composition

The sucrose, calcium sulfate dihydrate and a GABA uptake inhibitor shown in Table II below, are mixed and granulated in the proportions shown with a 10% gelatin solution. The wet granules are screened, dried, mixed with the starch, talc and stearic acid, screened and compressed into a tablet.

TABLE III

| INGREDIENTS | AMOUNTS |
|---|---|
| 1,2,5,6-tetrahydro-3-pyridinecarboxylic acid | 20 mg |
| Calcium sulfate dihydrate | 30 mg |
| Sucrose | 4 mg |
| Starch | 2 mg |
| Talc | 1 mg |
| Stearate acid | 0.5 mg |

While the above descriptions and examples fully describe the invention and the preferred embodiment thereof, it is understood that the invention is not limited to the particular disclosed embodiments coming within the scope of the following.

What is claimed is:

1. A method for treating cough in a mammal comprising administering to said mammal an anti-tussive effective amount of a compound that inhibits GABA uptake.

2. A method according to claim 1, wherein the GABA uptake inhibiting compound is administered at a dose of from about 0.01 mg/kg to about 20 mg/kg.

3. A method according to claim 1, wherein the GABA uptake inhibiting compound is administered at a dose of from about 0.1 mg/kg to about 5 mg/kg.

4. The method according to claim 2 wherein the GABA uptake inhibiting compound is (R)-1-(4,4-diphenyl-3-butenyl)-3-piperidinecarboxylic acid.

5. The method of claim 2 wherein the GABA uptake inhibiting compound is (R)-1-[4,4-bis(3-methyl-2-thienyl)-3-butenyl]-3-piperidinecarboxylic acid.

6. The method of claim 2 wherein the GABA uptake inhibiting compound is guvacine.

* * * * *